United States Patent
Chen et al.

(10) Patent No.: US 7,747,062 B2
(45) Date of Patent: Jun. 29, 2010

(54) METHODS, DEFECT REVIEW TOOLS, AND SYSTEMS FOR LOCATING A DEFECT IN A DEFECT REVIEW PROCESS

(75) Inventors: Da Chen, San Jose, CA (US); Christophe Fouquet, Sunnyvale, CA (US); Saibal Banerjee, Fremont, CA (US); Santosh Bhattacharyya, San Jose, CA (US); Joe Wang, Sunnyvale, CA (US); Lian Yao, Woodridge, IL (US); Mike van Riet, Morgan Hill, CA (US); Igor Germanenko, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 1038 days.

(21) Appl. No.: 11/270,771

(22) Filed: Nov. 9, 2005

(65) Prior Publication Data

US 2008/0032429 A1    Feb. 7, 2008

(51) Int. Cl.
*G06K 9/00* (2006.01)
(52) U.S. Cl. .................. 382/145; 382/141
(58) Field of Classification Search ............. None
See application file for complete search history.

(56) References Cited

U.S. PATENT DOCUMENTS

| | | | |
|---|---|---|---|
| 6,407,373 B1 | 6/2002 | Dotan | |
| 6,701,259 B2 | 3/2004 | Dor et al. | |
| 6,744,266 B2 | 6/2004 | Dor et al. | |
| 6,870,169 B2 * | 3/2005 | Obara et al. | 250/492.2 |
| 2004/0038454 A1 | 2/2004 | Coldren et al. | |
| 2005/0122508 A1 | 6/2005 | Uto et al. | |

OTHER PUBLICATIONS

International Search Report and Written Opinion for PCT/US06/60701 mailed on Aug. 1, 2008.

\* cited by examiner

*Primary Examiner*—Vikkram Bali
*Assistant Examiner*—Elisa M Rice
(74) *Attorney, Agent, or Firm*—Ann Marie Mewherter

(57) ABSTRACT

Methods, defect review tools, and systems for locating a defect in a defect review process are provided. One method includes acquiring one or more images and data from an inspection tool. The one or more images illustrate an area on a specimen in which a defect to be reviewed is located. The data indicates a position and features of the defect within the area. The method also includes acquiring one or more additional images of the specimen proximate the position of the defect indicated in the data using an imaging subsystem of a defect review tool. In addition, the method includes identifying a portion of the one or more additional images that corresponds to the one or more images. The method further includes determining a position of the defect within the portion of the one or more additional images using the data.

30 Claims, 6 Drawing Sheets

United States Patent US 7,747,062 B2

METHODS, DEFECT REVIEW TOOLS, AND SYSTEMS FOR LOCATING A DEFECT IN A DEFECT REVIEW PROCESS

BACKGROUND OF THE INVENTION

1. Field of the Invention

The present invention generally relates to methods, defect review tools, and systems for locating a defect in a defect review process. Certain embodiments relate to determining a position of a defect on a specimen using one or more images and data generated by an inspection tool and one or more additional images generated by an imaging subsystem of a defect review tool.

2. Description of the Related Art

The following description and examples are not admitted to be prior art by virtue of their inclusion in this section.

Inspection processes are used at various times during a semiconductor manufacturing process to detect defects on a specimen such as a reticle and a wafer. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices. Accordingly, much work in the inspection field has been devoted to designing inspection systems that can detect defects having sizes that were previously negligible.

Another important part of yield control is determining the cause of the defects on the wafer or reticle such that the cause of the defects can be corrected to thereby reduce the number of defects on other wafers or reticles. Often, determining the cause of the defects involves identifying the defect type and other characteristics of the defects such as size, shape, composition, etc. Since inspection typically only involves detecting defects on the wafer or reticle and providing limited information about the defects such as location, number, and sometimes size, defect review is often used to determine more information about individual defects than that which can be determined from inspection results. For instance, a defect review tool may be used to revisit defects detected on a wafer or reticle and to examine the defects further in some manner either automatically or manually. Defect review can also be used to verify that defects detected by inspection are actual defects instead of, for example, noise and nuisance events.

Some examples of commonly used defect review tools include high resolution optical imaging systems, scanning electron microscopes (SEMs) and less commonly transmission electron microscopes. In order to be successful, the defect review tool must be able to accurately find the defects that are to be reviewed. For instance, if the defect review tool determines an incorrect location for a defect, during review at the incorrect position the defect review tool field of view (FOV) may be located on a non-defective portion of the specimen or a portion of a specimen containing a different defect. In this manner, when the defect review tool is erroneously positioned above a non-defective portion of the specimen, the defect review tool may determine that the detected defect is not an actual defect. Alternatively, if the defect review tool is erroneously positioned above a different defect on the specimen, the defect review results for the reviewed defect may be assigned to the wrong detected defect. As such, if the defect review tool cannot accurately find the defects that are to be reviewed, the defect review results may be substantially inaccurate and without user intervention (e.g., manually reviewing the defect review results) such inaccuracies may be largely undetected. Therefore, if the results of defect review are used to monitor and control semiconductor fabrication processes, the monitor and control may be ineffective or possibly even detrimental to the performance of the semiconductor fabrication processes.

Finding the defects in a defect review process is not trivial for a number of reasons. For instance, different coordinate sets are involved in determining the coordinates of the defect with respect to the FOV of the defect review tool. One set of coordinates is the set of coordinates in which the defect location is reported by the inspection tool that detected the defect. The defect location coordinates may be referenced to the inspection tool stage coordinates and translated such that the defect coordinates are referenced to the center of the specimen. An additional set of coordinates is the set of coordinates of the specimen with respect to the stage of the defect review tool. Since the specimen is typically moved from the inspection tool to the defect review tool, the coordinates of the specimen reported by the inspection tool will need to be translated to the review tool stage coordinates. During this coordinate mapping, there are systematic and random errors that need to be corrected before the review tool can locate the defect.

A number of different methods and systems have been developed to improve the defect finding step of defect review processes. To eliminate the systematic errors, normally wafer alignment, die corner registration, and defect coordinate deskew steps are performed. However, there are still random errors in the defect coordinates that are caused by the defect detection technology (such as technology for imaging or collecting scattered light from the defect) and defect location calculation and interpolation. In addition, different thermal conditions in the inspection tool during the defect detection and in the defect review tool during defect review may produce random error in the defect coordinates. One method to eliminate this random error that is commonly referred to as automatic defect locating (ADL) is performed using the defect review subsystem of the defect review tool. ADL may include generating a low resolution image (or large FOV image) of a specimen at approximately the location of a defect reported by the inspection tool using an optical microscope (OM) or a SEM of a defect review tool. The defect may then be redetected in the low resolution image. For instance, the large FOV image can be compared to a reference image to detect the defect in the low resolution image. A small FOV image of the defect may then be captured which is commonly used for defect classification purposes.

Such methods have a number of disadvantages. For instance, the FOV on the specimen during ADL is dependent on the defect coordinate inaccuracy of the inspection tool that inspected the specimen. In one such example, if the coordinates of the defect reported by the inspection tool are substantially inaccurate, then the FOV used for the low resolution imaging may need to be large enough to ensure that the defect is located in the image, but so large that defect redetection (particularly for relatively small defects) may not be possible or will take a relatively long time to perform. In addition, the sensitivity of ADL is limited by the parameters used for ADL including the FOV, pixel density, image integration time, noise in the image including specimen charging effects in SEM images, and the redetection algorithm that is used. Furthermore, ADL performed using SEM images will not be able to redetect defects that are inherently not visible to the SEM such as defects that are located below an upper surface of the specimen. Moreover, ADL performed using SEM images may also have a low redetection success rate for other types of defects such as low contrast defects, defects that are overwhelmed by unpredictable noise generated in the images, and defects that are too small to be redetected in low resolution SEM images.

An additional disadvantage of currently used methods and systems is that during ADL, imaging of the specimen by the SEM may cause contamination of each area that is imaged (e.g., both a defect die and a reference die). In addition, if all defect redetecting functions are performed in electron beam mode, then such repeated exposure of the specimen to the electron beam increases the potential for surface contamination and damage. The specimen must also be imaged at least twice by the SEM: at least once during ADL, and again during review. Therefore, such repeated exposure to the electron beam may increase the probability of damage to and contamination of the specimen. Furthermore, in order to mitigate the effects of ADL on the throughput of the defect review process, the low resolution imaging by the SEM may be performed with relatively high current and landing energy. Therefore, the portions of the specimen imaged during ADL may be subjected to conditions that are more likely to cause damage to and contamination of the specimen.

A different apparatus for reviewing defects on an object is illustrated in U.S. Pat. No. 6,407,373 to Dotan, which is incorporated by reference as if fully set forth herein. As described by Dotan, the apparatus includes a stage for receiving the object thereon, and both an OM and a SEM. The OM is used to redetect previously mapped defects on the object surface. Once the defect has been redetected, a translation system moves the stage a predetermined displacement such that the defect is positioned for review by the SEM.

Since the apparatus of Dotan does not use the SEM to redetect defects, the apparatus described by Dotan is less likely to cause electron damage and contamination of the specimen than the ADL methods described above. However, redetecting the defect as described by Dotan is disadvantageous for a number of reasons. For instance, such redetection may be quicker than the inspection process since only the positions in the defect map produced by inspection that indicate a potential defect are examined by the OM of the defect review apparatus. However, the defects still have to be redetected, which may limit the throughput, sensitivity, and accuracy of the defect location of the defect review process.

The apparatus disclosed by Dotan also has some of the disadvantages of ADL described above. For instance, the FOV on the specimen during the redetection described by Dotan is dependent on the defect coordinate inaccuracy of the inspection tool that inspected the specimen, which is disadvantageous as described further above. In addition, like ADL, the sensitivity of the defect redetection disclosed by Dotan is limited by the parameters of the OM including the FOV, the pixel density, and the redetection algorithm. Furthermore, most of the time, the imaging mode of the defect review tool is substantially different from the imaging mode used by the inspection tool to detect the defects. As a result of using this ADL method, there is no guarantee that the redetected defects in the FOV of the defect review tool are the same defects that are reported by the inspection tool. This error will cause false defect classification and incorrect defect root cause analysis.

Accordingly, it may be advantageous to develop methods, defect review tools, and systems for locating a defect in a defect review process that are independent of the defect coordinate accuracy of an inspection tool, are not limited by the parameters of the imaging subsystem used to image the specimen during defect locating, do not cause charging and/or contamination of the specimen during defect locating, and do not reduce the throughput of the defect review process.

SUMMARY OF THE INVENTION

The following description of various embodiments of methods, defect review tools, and systems is not to be construed in any way as limiting the subject matter of the appended claims.

One embodiment relates to a method for locating a defect in a defect review process. The method includes acquiring one or more images and data from an inspection tool. The one or more images illustrate an area on a specimen in which a defect to be reviewed is located. The data indicates a position and features of the defect within the area. The method also include acquiring one or more additional images of the specimen proximate the position of the defect indicated in the data using an imaging subsystem of a defect review tool. In addition, the method includes identifying a portion of the one or more additional images that corresponds to the one or more images. The method further includes determining a position of the defect within the portion of the one or more additional images using the data.

In one embodiment, the method includes identifying the defect using information within a database. The information was generated by the inspection tool. In another embodiment, the one or more images include one or more bright field (BF) images, one or more dark field (DF) images, one or more laser DF images, one or more scanning electron microscope (SEM) images, or some combination thereof. In an additional embodiment, the data includes one or more other images that illustrate the position and the features of the defect within the area. In some embodiments, the one or more additional images include one or more BF images, one or more DF images, one or more laser DF images, one or more SEM images, or some combination thereof.

In one embodiment, acquiring the one or more images and the data from the inspection tool is performed by the defect review tool. In another embodiment, the defect review tool and the inspection tool, in combination, are configured as an information on-demand system. In some embodiments, the imaging subsystem is configured as an optical subsystem. In an additional embodiment, the defect review tool is configured as a SEM.

In some embodiments, the method includes determining a position of the defect with respect to the defect review tool from the position of the defect within the portion of the one or more additional images such that the defect can be positioned within a field of view (FOV) of the defect review tool. In another embodiment, the one or more images illustrate patterned features on the specimen. In one such embodiment, the data includes one or more other images that do not illustrate the patterned features on the specimen. In a further embodiment, the identifying step of the method includes comparing all patterned features illustrated in the one or more images with patterned features illustrated in different portions of the one or more additional images. In yet another embodiment, the identifying step includes comparing all pattern features and defect features illustrated in the one or more images with patterned features and defect features illustrated in different portions of the one or more additional images.

In some embodiments, the identifying step includes determining if multiple portions of the one or more additional images correspond to the one or more images and comparing the multiple portions with each other at the position indicated in the data to identify the multiple portion in which the defect is located. In another embodiment, the identifying step includes determining if multiple portions of the one or more additional images correspond to the one or more images. In one such embodiment, the data includes one or more other images. In addition, the identifying step includes comparing the multiple portions with the one or more other images at the position of the defect illustrated in the one or more other images to identify the multiple portion in which the defect is located.

In another embodiment, the method includes verifying the position of the defect within the portion by acquiring one or more other images at the position of the defect within the portion. In such an embodiment, an image type of the one or more additional images is different than an image type of the one or more other images. Each of the embodiments of the method described above may include any other step(s) described herein.

Another embodiment relates to a defect review tool configured to locate a defect in a defect review process. The defect review tool includes a processor configured to acquire one or more images and data from an inspection tool. The one or more images illustrate an area on a specimen in which a defect to be reviewed is located. The data indicates a position and features of the defect within the area. The defect review tool also includes an imaging subsystem configured to acquire one or more additional images of the specimen proximate the position of the defect indicated in the data. The processor is also configured to identify a portion of the one or more additional images that corresponds to the one or more images and to determine a position of the defect within the portion of the one or more additional images using the data.

In one embodiment, the processor is configured to identify the defect using information within a database. The information was generated by the inspection tool. In another embodiment, the one or more images include one or more BF images, one or more DF images, one or more laser DF images, one or more SEM images, or some combination thereof. In an additional embodiment, the data includes one or more other images that illustrate the position and the features of the defect within the area. In some embodiments, the one or more additional images include one or more BF images, one or more DF images, one or more laser DF images, one or more SEM images, or some combination thereof.

In one embodiment, the defect review tool and the inspection tool, in combination, are configured as an information on-demand system. In another embodiment, the imaging system is configured as an optical subsystem. In some embodiments, the defect review tool includes a defect review subsystem configured as a SEM. In a further embodiment, the processor is configured to detect a position of the defect with respect to a defect review subsystem from the position of the defect within the portion of the one or more additional images such that the defect can be positioned within a FOV of the defect review subsystem.

In an additional embodiment, the one or more images illustrate patterned features on the specimen. In one such embodiment, the data includes one or more other images that do not illustrate the patterned features on the specimen. In some embodiments, the processor is configured to identify the portion of the one or more additional images that corresponds to the one or more images by comparing all patterned features illustrated in the one or more images with patterned features illustrated in different portions of the one or more additional images. In other embodiments, the processor is configured to identify the portion of the one or more additional images that corresponds to the one or more images by comparing all patterned features and defect features illustrated in the one or more images with patterned features and defect features illustrated in different portions of the one or more additional images.

In one embodiment, the processor is configured to identify the portion of the one or more additional images that corresponds to the one or more images by determining if multiple portions of the one or more additional images correspond to the one or more images and comparing the multiple portions with each other at the position indicated in the data to identify the multiple portion in which the defect is located. In another embodiment, the data includes one or more other images. In one such embodiment, the processor is configured to identify the portion of the one or more additional images that corresponds to the one or more images by determining if multiple portions of the one or more additional images correspond to the one or more images and comparing the multiple portions with the one or more other images at the position illustrated in the one or more other images to identify the multiple portion in which the defect is located.

In one embodiment, the imaging subsystem is configured to acquire one or more other images at the position of the defect within the portion. In one such embodiment, an image type of the one or more additional images is different than an image type of the one or more other images. In such embodiments, the processor may be configured to verify the position of the defect within the portion using the one or more other images. Each of the embodiments of the system described above may be further configured as described herein.

An additional embodiment relates to a system configured to locate a defect in a defect review process. The system includes an inspection tool configured to generate one or more images that illustrate an area on the specimen in which a defect to be reviewed is located and data that indicates a position and features of the defect within the area. The system also includes a defect review tool configured to acquire the one or more images and the data from the inspection tool. The defect review tool is also configured to generate one or more additional images of the specimen proximate the position indicated in the data. In addition, the defect review tool is configured to identify a portion of the one or more additional images that corresponds to the one or more images. The defect review tool is further configured to determine a position of the defect within the portion of the one or more additional images using the data. This system embodiment may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
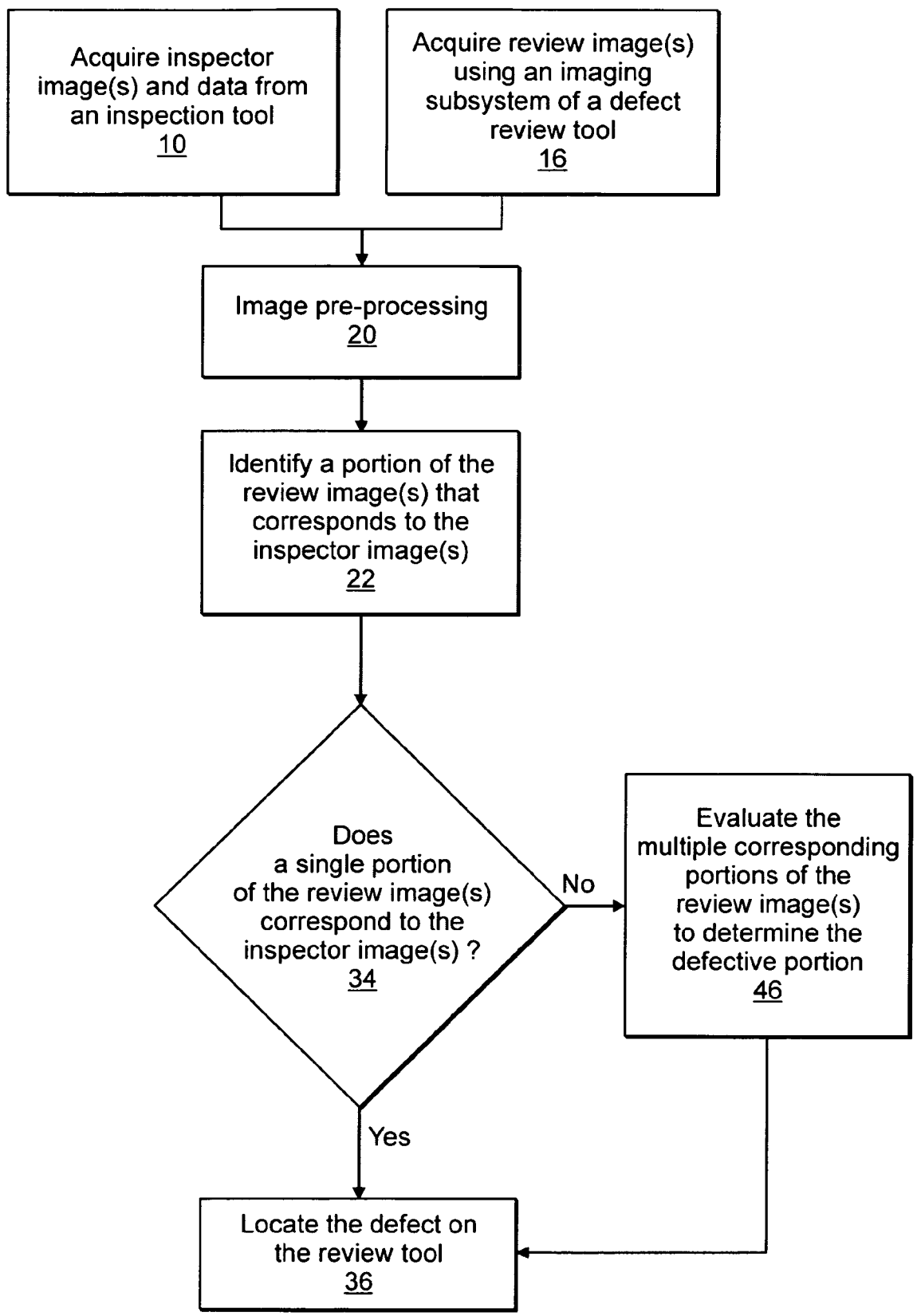
FIG. 1 is a flow chart illustrating one embodiment of a method for locating a defect in a defect review process.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" refers to a reticle or a wafer. The terms "reticle" and "mask" are used interchangeably herein. A reticle generally includes a transparent substrate such as glass, borosilicate glass, and fused silica having opaque regions formed thereon in a pattern. The opaque regions may be replaced by regions etched into the transparent substrate. Many different types of reticles are known in the art, and the term reticle as used herein is intended to encompass all types of reticles.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities. A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates one embodiment of a method for locating a defect in a defect review process. It is noted that all of the steps shown in FIG. 1 are not essential to practice of the method. One or more steps may be omitted from or added to the method shown in FIG. 1, and the method can still be practiced within the scope of the embodiments described herein.

As shown in step 10 of FIG. 1, the method includes acquiring one or more images (hereinafter "inspector image(s)") and data (hereinafter "inspector data") from an inspection tool. The inspector image(s) illustrate an area on a specimen in which a defect to be reviewed is located. The inspector image(s) may include one or more bright field (BF) images, one or more dark field (DF) images, one or more laser DF images, one or more scanning electron microscope (SEM) images, or some combination thereof. The inspector data indicates a position and features of the defect within the area. In some embodiments, the inspector data may include image data. In one such embodiment, the inspector data includes one or more other images (hereinafter "additional inspector image(s)") that illustrate the position and the features of the defect within the area.

Figure 2:
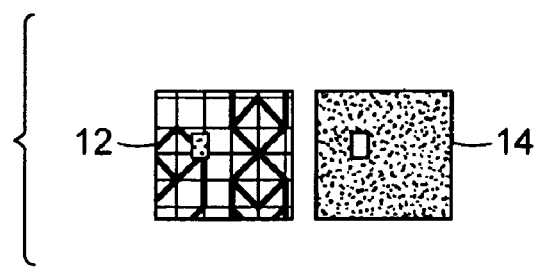
FIG. 2 includes schematic diagrams illustrating a top view of examples of one or more images and data that may be acquired from an inspection tool.

FIG. 2 includes examples of such inspector image(s) and additional inspector image(s). In particular, inspector image 12 is an example of an image of a specimen that may be generated by an inspection tool during inspection of the specimen. Inspector image 12 illustrates an area on the specimen in which a defect to be reviewed is located. This specimen is a wafer having patterned features formed thereon. Inspector image 12 illustrates the patterned features on the specimen. One example of an inspection tool that can generate such an inspector image is a BF inspection tool. As further shown in inspector image 12, the inspector image illustrates a relatively small portion of the specimen. In particular, the inspector image may be a "patch image" generated by the inspection tool. A "patch image" can be generally defined as an image that is "grabbed" by the inspection tool. In addition, the inspector image may be generated by the inspection tool during the inspection of the specimen (i.e. "run-time" images).

Additional inspector image 14 illustrates a position and features of a defect within the area defined by inspector image 12. In particular, the defect appears as the bright spot in additional inspector image 14. Additional inspector image 14, in this example, does not illustrate the patterned features on the specimen that are illustrated in inspector image 12. In particular, additional inspector image 14 may be a difference image that was generated by subtracting a reference image from inspector image 12. The reference image may be another image of the specimen generated by the inspection tool at a position on the specimen at which the features in inspector image 12 are also formed. Alternatively, the reference image may be an image of the specimen generated (or "rendered") from a database containing information about the features formed on the specimen. In any case, the reference image may be subtracted from inspector image 12, and any differences between the images may be used to detect defects on the specimen.

The inspector image(s) and inspector data may be acquired from an inspection tool in a number of different manners. In one embodiment, acquiring inspector image(s) and inspector data from the inspection tool is performed by the defect review tool that will perform the defect review process. In another embodiment, the defect review tool and the inspection tool, in combination, are configured as an information on-demand system, which is described in further detail herein. For instance, the defect review tool may send a request for the inspector image(s) and inspector data to the inspection tool. The defect review tool may then receive the requested inspector image(s) and inspector data from the inspection tool. In addition, the defect review tool may receive only the inspector image(s) and inspector data that were requested from the inspection tool. In this manner, the defect review tool may not receive all of the defect information and images of the specimen that were generated during inspection. In addition to the inspector image(s) and inspector data, the defect review tool may also request defect and other information from the inspection tool such as inspection optical mode, pixel size, illumination levels, defect sizes, and other defect features. Such requesting and receiving of defect information, inspector image(s), and inspector data may be performed in any manner known in the art.

Prior to requesting such inspector image(s) and inspector data from an inspection tool, the method may include determining which defects are to be reviewed. For instance, the method may include identifying one or more defects to be reviewed using information within a database. The information in the database may have been generated by the inspection tool. For instance, an inspection tool may be configured to generate inspection results in the form of a Klarity Results File (KLARF) or any other file that can be created and read by multiple differently configured tools. The file may then be sent to a database such as a defect database or a fab database. The defect database may include inspection results generated for a number of different specimens. The defect database may also include inspection results that were generated by a number of different inspection tools. A fab database may include information generated by a number of different tools in a fab (e.g., inspection tools, metrology tools, defect review tools, process tools, etc.).

The inspection results may include a variety of information such as a specimen identity and a defect list containing information about the defects detected by the inspection tool. In this manner, upon receiving or determining the identity of the specimen on which defects are to be reviewed, the defect review tool may access the inspection results for that specimen. In some embodiments, identifying the defect or defects to be reviewed may include selecting the defects on the specimen that are to be reviewed (which is commonly referred to as "defect sampling") using the inspection results from the database. Such defect sampling may be performed by the inspection tool or the defect review tool. In this manner, the inspector image(s), inspector data, and any other information may be acquired for only the defects selected by sampling.

As shown in step 16 of FIG. 1, the method also includes acquiring one or more additional images (hereinafter "review image(s)") of the specimen proximate the position of the defect indicated in the inspector data using an imaging subsystem of a defect review tool. In one embodiment, the imaging subsystem is configured as an optical subsystem. In an additional embodiment, the imaging subsystem may be configured for BF, DF, or laser DF imaging. In another embodiment, the imaging subsystem is configured as a SEM. In some embodiments, the review image(s) include one or more BF images, one or more DF images, one or more laser DF images, one or more SEM images, or some combination thereof. The imaging subsystem and the defect review tool may be configured as described further herein.

Figure 3:
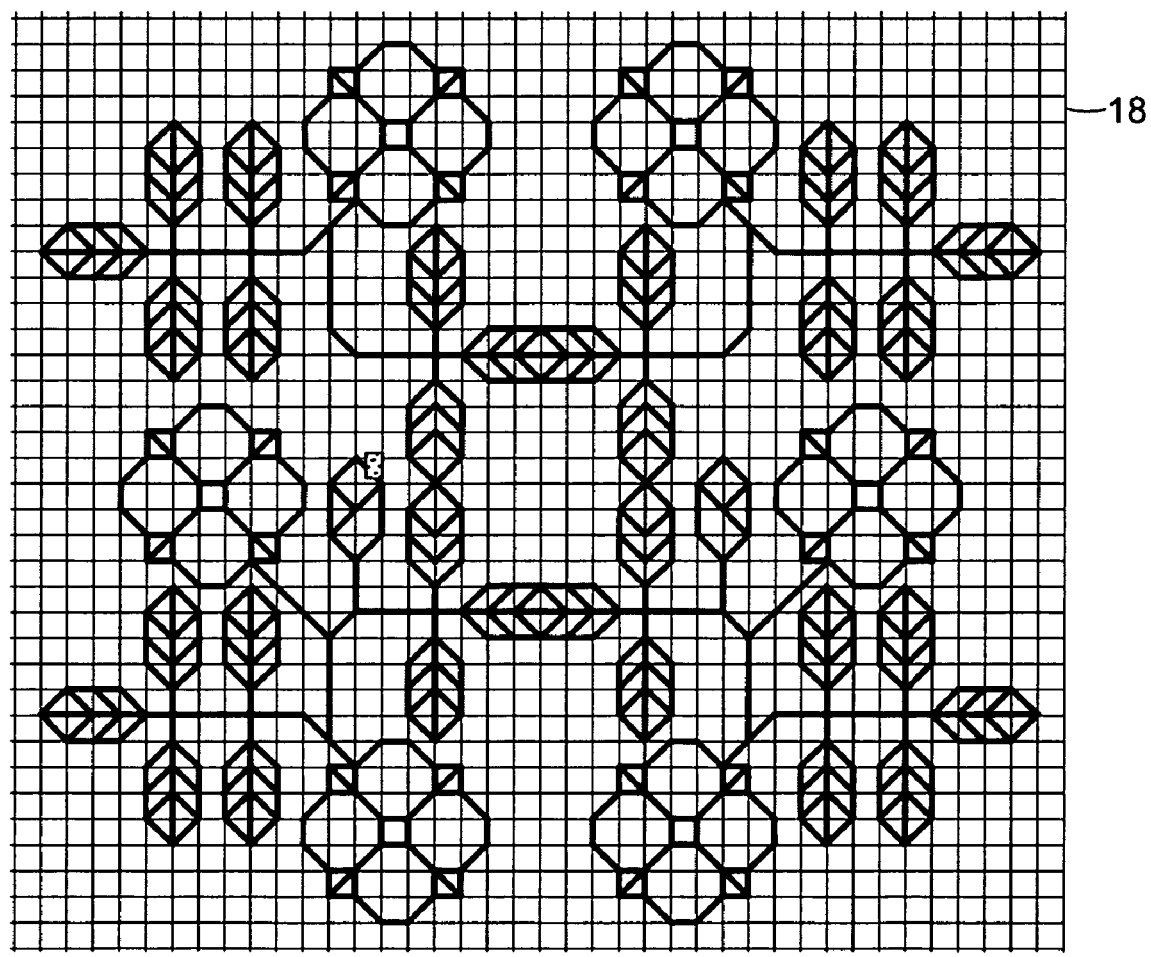
FIG. 3 is a schematic diagram illustrating a top view of an example of one or more additional images that may be acquired using an imaging subsystem of a defect review tool.

FIG. 3 is one example of a review image of the specimen, for which the inspector image and inspector data are illustrated in FIG. 2. Review image 18 may be acquired by an imaging subsystem that may be incorporated into a defect review tool. In one example, the imaging subsystem that is used to acquire the review image(s) may be a BF optical microscope (OM). Patterned features formed on the specimen are illustrated in review image 18. In addition, the review image illustrates features across a much larger area on the specimen than inspector image 12. In this manner, the review image may have been generated by an imaging subsystem that has a much larger field of view (FOV) than the FOV of the inspection tool which generated inspector image 12. In this manner, the review image may be a relatively low resolution image of the specimen since such an image has sufficient resolution for the defect relocation steps described herein.

In one such example, the imaging subsystem may have a magnification that is lower than that of the inspection tool. Otherwise, the imaging subsystem and the inspection tool may be similarly configured. For instance, the imaging subsystems included in the defect review tool and the inspection tool may have similar parameters such as wavelength(s) of illumination, angle(s) of incidence, angle(s) of collection, detector configurations, etc. Such similarities in the imaging subsystems may reduce the potential for error in further steps of the method described herein. However, the methods described herein may include accounting for differences in the imaging subsystems such as different pixel sizes and different illumination wavelengths. In this manner, the methods may have a high degree of flexibility as to the different tools and subsystems that can be used to perform the methods.

In some embodiments, the method includes image pre-processing, as shown in step 20 of FIG. 1. Image pre-processing may include image pre-processing of the inspector image(s) and the review image(s) acquired in steps 10 and 16, respectively, shown in FIG. 1. Image pre-processing may include matching the pixel size of the inspector and review images. In one embodiment, matching the pixel sizes of the inspector and review images may be performed using bilinear interpolation for geometric scaling. In other embodiments, matching the pixel sizes of the inspector and review images may be performed using bicubic interpolation, b-spline and other spline based interpolation techniques, or any other suitable technique known in the art. In addition, the image pre-processing may include matching the grey levels and contrast of the inspector and review images. Matching the grey levels and contrasts of the inspector and review images may include determining the mean and standard deviation of the selected inspector image or images, determining gain and offset values based on the mean and standard deviation, and applying the gain and offset values to the additional image or images from the review tool to produce review image(s) that have similar brightness and contrast as the inspector image(s). In another example, matching of the grey levels and contrast of the inspector and review images may include histogram matching, histogram percentile value matching, or any other suitable method or algorithm known in the art.

Figure 4:
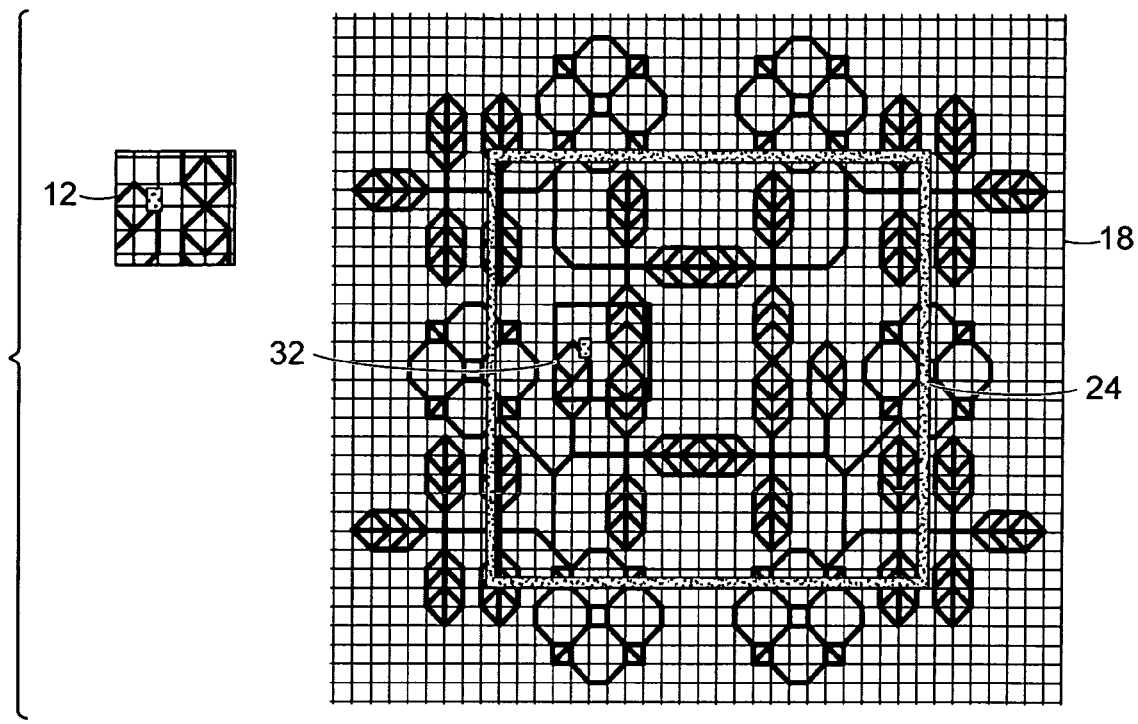
FIG. 4 is a schematic diagram illustrating a top view of an example of a portion of the one or more additional images of FIG. 3 that corresponds to the one or more images of FIG. 2.

As shown in step 22 of FIG. 1, the method also includes identifying a portion of the review image(s) that corresponds to the inspector image(s). For instance, as shown in FIG. 4, search window 24 may be located within review image 18. Characteristics of the review image within search window 24 and characteristics of inspector image 12 may be compared to determine if a portion of review image 18 within search window 24 corresponds to the inspector image. The characteristics that are compared may include characteristics of the features in the review image within the search window and features illustrated in the inspector image.

In one embodiment, identifying the portion of the review image(s) that corresponds to the inspector image(s) includes comparing all patterned features illustrated in the inspector image(s) with patterned features illustrated in different portions of the review image(s). In this manner, all of the features within the inspector image(s) may be used in the comparison such that the portion of the review image(s) that corresponds to the inspector image(s) is determined with relatively high accuracy. In addition, all of the features within the inspector image(s) may be compared with features illustrated in different portions of the review image(s) within the search window. In another embodiment, identifying the portion of the review image(s) that corresponds to the inspector image(s) includes comparing all patterned features and defect features illustrated in the inspector image(s) with patterned features and defect features illustrated in different portions of the review image(s). For example, if the defect is apparent in the inspector image(s), the defect in combination with other features in the inspector image(s) may be compared with features in the review image(s). Therefore, the defect is treated as a feature in the inspector image(s). In this manner, defect relocation involves pattern matching, not redetection of the defect, and the defect may be considered as part of the pattern that is matched.

As shown in FIG. 4, the dimensions of search window 24 are larger than the dimensions of inspector image 12 (taking into account the differences in the magnifications of the inspector and review images). The size of the search window may also directly correlate to the defect coordinate inaccuracy of the inspection tool. Different inspection tools have different expected defect coordinate inaccuracies. Therefore, the size of the search window may be different for different inspection tools. The error in the defect coordinate inaccuracy may also include both systematic and random errors of the inspection and review tools. The search window may also be larger at the beginning of the identifying step because at that point there are more uncertainties in the defect location. However, once at least some defect coordinates are corrected based on the defects relocated by the review tool, the certainty of the remaining defect locations increases. Therefore, the dimensions of the search window may be reduced accordingly.

The position of the search window within the review image(s) during the identification step may also vary. For instance, the position of the search window may be determined arbitrarily such that the search window is located at the same position in each review image. In one such example, assuming that a review image is centered on the defect coordinates reported by the inspection tool, the position of the search window may be centered on the review image. Alternatively, the position of the search window may be determined randomly. In another alternative, the position of the search window may be determined based on characteristics of the review image(s). For instance, the method may involve searching the entire review image(s) for one or more features contained within the inspector image(s). In this manner, the method may be able to roughly determine the probability that an inspector image corresponds to different portions of a review image and may eliminate the low probability portions of the review image from consideration during the identification step. In addition, the search window may be positioned such that it contains a portion of the review image that has a relatively high probability of corresponding to the inspector image.

Figure 5:
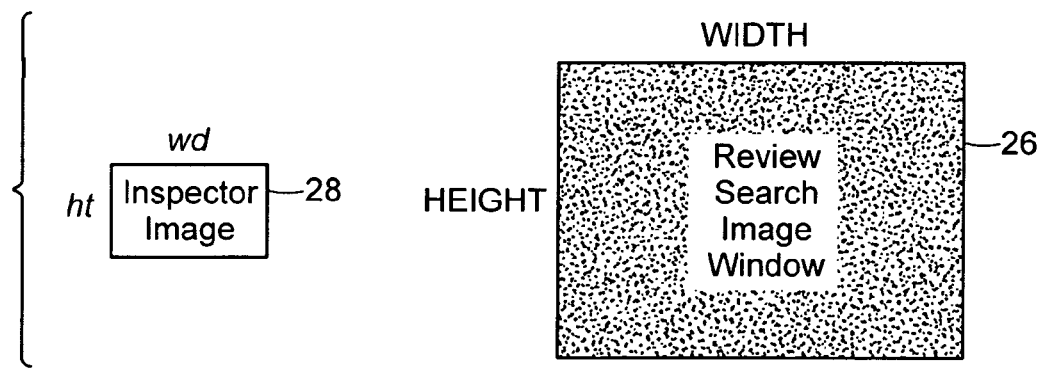
FIG. 5 includes schematic diagrams illustrating a top view of one example of an image that may be acquired from an inspection tool and one example of a search window that may be located within an additional image that is acquired using an imaging subsystem of a defect review tool.
Figure 6:
FIG. 6 is a schematic diagram illustrating one location of the image acquired from the inspection tool of FIG. 5 within the search window of FIG. 5.

In one embodiment, identifying the portion of the review image(s) that corresponds to the inspector image(s) as shown in step 22 of FIG. 1 includes one or more steps such as registration of the review and inspector images, measuring a match between the review and inspector images, using edges of the review and inspector images for matching, and peak isolation. Registration of the review and inspector images may be performed to identify locations of the inspector image(s) that match the review image(s). As shown in FIG. 5, the dimensions (e.g., the height and the width) of search window 26 are larger than the dimensions (e.g., the height and the width) of inspector image 28. As shown in FIG. 6, inspector image 28 may be positioned within search window 26. In addition, inspector image 28 may be moved (e.g., translated) to every possible location in the search window. At each possible location of the inspector image within the search window, a match measurement may be performed for the inspector image and the sub-image (i.e., that portion of the review image) that the inspector image overlaps. The match measurements may be recorded in a two-dimensional plane (corresponding to the locations of the inspector image within the search window) and is often referred to as a "correlation surface." The better the match between the inspection and review images at a location, the higher the match measurement at that location. Hence, peaks in the correlation surface correspond to good matches between the inspection and review images.

Figure 7:
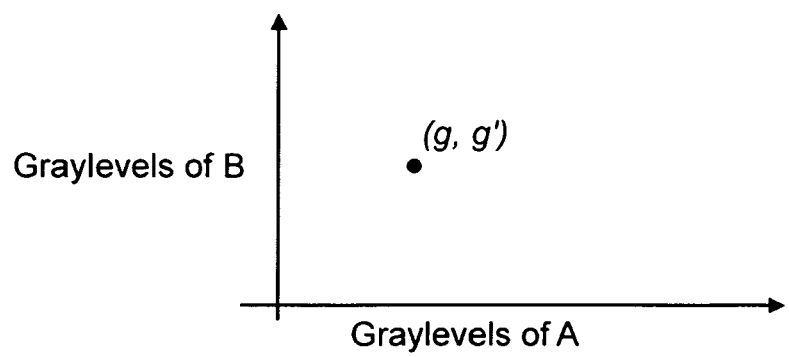
FIG. 7 is a two-dimensional plot illustrating the grey levels of two images A and B at an initial location within the images.
Figure 8:
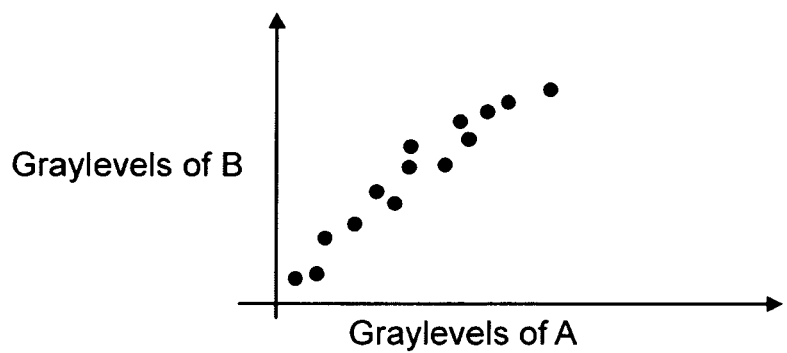
FIG. 8 is a two-dimensional plot illustrating the grey levels of the images A and B at additional locations within the images.

In another example, given two images A and B having the same dimensions or processed to have the same dimensions, measuring a match between the images may include letting (g, g') be the grey levels of images A and B, respectively, at location (0,0). This point may be plotted in a two dimensional plot such as the plot shown in FIG. 7. Additional such points may be plotted that represent the grey levels of images A and B at additional corresponding locations within the images. The grey levels of the two images at all corresponding locations within the images may be plotted. Such a plot may be generally referred to as a "scattergram." The final plot generated by this step may appear similar to the plot shown in FIG. 8. How well images A and B match may then be determined using the properties of the scattergram. In particular, if images A and B match exactly, (e.g., grey level for grey level at every location), then the scatterplot may be a substantially perfect line having a 45° slope. There are many ways to perform matching using the scattergram data. In one embodiment, the degree of matching may be determined using not only the linearity of the scattergram data but also the slope (where a 45° slope represents an ideal match). This approach enables match measurements to be more robust to noise and image distortions and provides better quality matching peaks.

As mentioned above, edge images may be used for identifying matches between inspector and review images. For example, to improve the reliability of the matching step, the edge or gradient-magnitude images of the inspector image(s) and the review image(s) may also be matched by the process described above. To form the gradient image of a given image, the original image may be convolved with a gradient filter. Suitable gradient filters for such a step include the Sobel filter and any other gradient filter known in the art. Gradients have both magnitude and direction. The edge image is the gradient-magnitude image.

As further mentioned above, peak isolation may be used to identity matches between the inspector image(s) and the review image(s). For example, multiple matches may be identified at different locations of the inspector images within the search window. In such an example, the exact locations of multiple matches may also be identified. In one embodiment, all peaks in the correlation surface that have values above a predetermined percentage of the globally maximum peak may be selected as matches. In another embodiment, non-maximum suppression may be used to set all values around a peak in the correlation surface to zero thereby aiding in identifying the locations of high peaks that correspond to a match.

The identification of matches between the inspector image(s) and the review image(s) may also include a number of further enhancements such as weighting the correlation surface using a centrally symmetric flat-top Gaussian function such that locations that are distant from the center have a lower likelihood of being identified as a good match.

Figure 9:
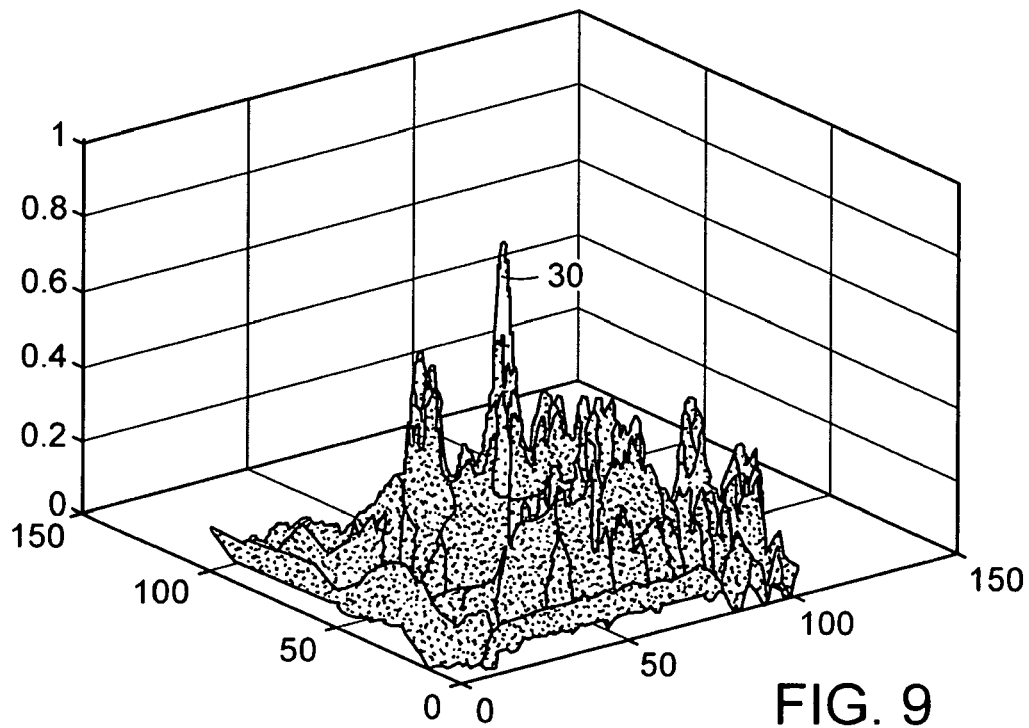
FIG. 9 is a three-dimensional plot illustrating the peak correlation values for the one or more images and one or more additional images shown in FIG. 4 across a search window.

By comparing the inspector image(s) and the review image(s) as described herein, the correlation of the inspector image(s) within the search window of the review image(s) can be determined. As shown in the plot of FIG. 9, single high correlation peak 30 indicates the position within the search window having the best correlation with the inspector image(s). As shown in FIG. 4, this high correlation peak corresponds to portion 32 of review image 18 within search window 24 that is determined to correspond to inspector image 12. Even if a perfect match of the inspector image is found in the review image, normal patterns of the specimen and the defect cannot be distinguished from one another. In this manner, additional inspector image 14 shown in FIG. 2, which is the difference image corresponding to inspector image 12, is used to identify the position of the defect within the portion of the review image that matches the inspector image. In this manner, the defect location can be derived from the additional inspector image(s) after the best correlation of the inspector and the review images has been identified.

The method, therefore, includes determining a position of the defect within the portion of the review image(s) using the inspector data. For instance, after portion 32 of review image 18 has been identified, the method may include overlaying additional inspector image 14 (shown in FIG. 2) with portion 32 of review image 18. In this manner, the position at which the bright spot corresponding to the defect shown in additional inspector image 14 overlaps with portion 32 of review image 18 indicates the location of the defect within portion 32. In another example, the method may include determining the coordinates of the bright spot within additional inspector image 14. In this manner, after portion 32 of review image 18 has been identified, the method may include identifying the coordinates within the portion of the review image that correspond to the coordinates of the bright spot within additional inspector image 14 as the location of the defect within the portion of the review image. As described above, therefore, the method determines the position of the defect within the review image(s), not by redetecting the defect as in previously used methods, but from the position of the defect in inspector data. In this manner, the defect does not have to be imaged in the review image(s) for redetection purposes.

As shown in step 34 of FIG. 1, the method may include determining if a single portion of the review image(s) was determined to correspond to the inspector image(s). If a single portion of the review image(s) was determined to correspond to the inspector image(s), the method may include locating the defect on the review tool as shown in step 36 of FIG. 1, which may be performed as described herein. One example in which a single solution is identified by determining a portion of review image(s) that corresponds to inspector image(s) is illustrated in the embodiments described above with respect to the images shown in FIGS. 2-4 since only one portion of review image 18 is determined to correspond to the inspector image. However, when a specimen contains repeatable pattern features, it may be possible that multiple portions of the review image(s) may be determined to correspond to inspector image(s).

In one embodiment, identifying a portion of review image(s) that corresponds to the inspector image(s) includes determining if multiple portions of the review image(s) correspond to the inspector image(s). In this manner, after finding one portion of the review image(s) that corresponds to the inspector image(s), the identification step is not terminated. Instead, all portions of the review image(s) are evaluated to determine if more than one portion corresponds to the inspector image(s). The multiple portions may be determined to correspond to the inspector image(s) if they have a correlation peak that is above some predetermined value (e.g., greater than about 0.6) and/or meet some criteria (e.g., location close to the expected defect location, etc.)

Figure 10:
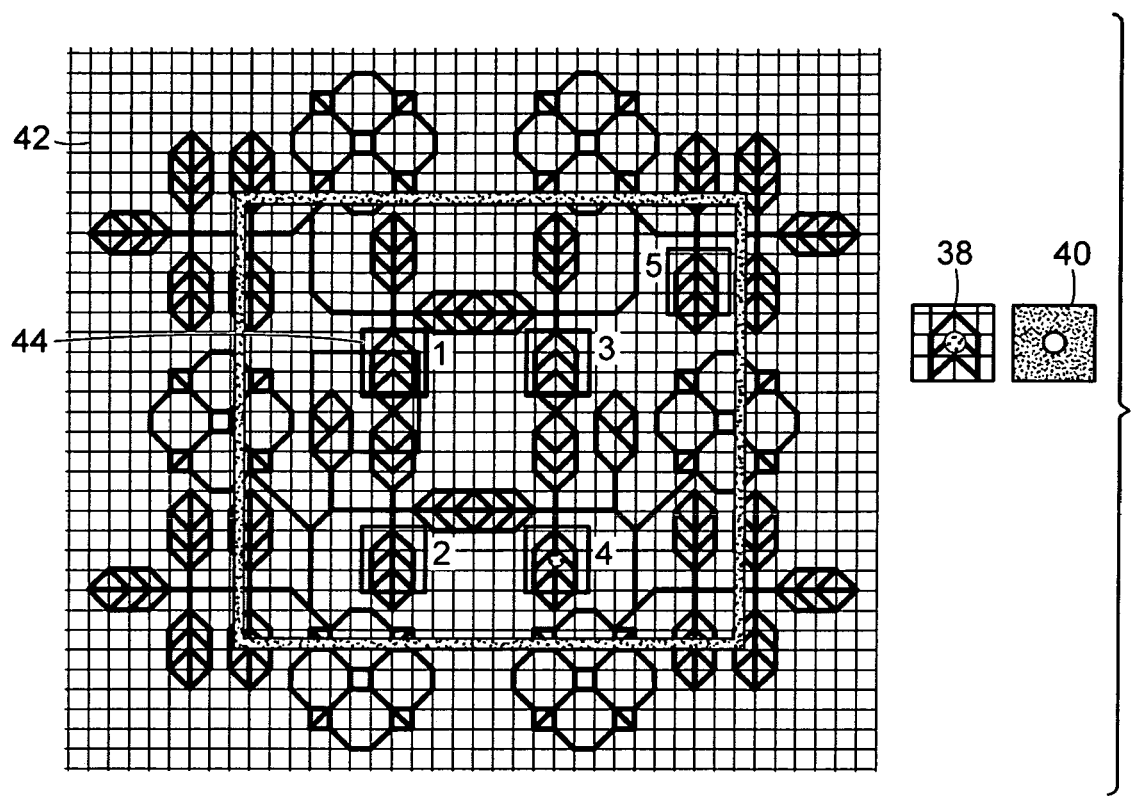
FIG. 10 includes schematic diagrams illustrating a top view of examples of one or more images and data that may be acquired from an inspection tool, one or more additional images that may be acquired using an imaging subsystem, and multiple portions of the one or more additional images that correspond to the one or more images.

In one example of such an embodiment, FIG. 10 illustrates examples of inspector image 38 and additional inspector image 40, which may be acquired as described herein. Identifying a portion of review image 42 that corresponds to the inspector image was performed as described above. For instance, such an identifying step may include pattern matching of the patch image from the inspection tool with the imaging subsystem image. As shown in review image 42, multiple portions 44 were determined to correspond to inspector image 38. In this manner, multiple identically matched patterns are identified within the search window of the review image, and each portion of the review image that matched the inspector image may be defined as a "block."

As shown in review image 42, five multiple portions were determined to correspond to the inspector image. However, in other instances, two or more multiple portions may be determined to correspond to the inspector image. In addition, although one particular arrangement of the multiple portions is shown in FIG. 10, it is to be understood that the multiple portions may be located at any positions within the review image. Since multiple portions of review image 42 were determined to correspond to the inspector image, it is desirable to determine the multiple portion in which the defect is located. In other words, it will be desirable to identify which of the multiple portions actually corresponds to the inspector image(s). Therefore, as shown in step 46 of FIG. 1, when multiple portions of the review image(s) were determined to correspond to the inspector image(s), the method may include evaluating the multiple corresponding portions of the review image(s) to determine the defective portion.

In one such embodiment, the method includes comparing the multiple portions with each other at the position of the defect indicated in the inspector data to identify the multiple portion in which the defect is located. In other words, the multiple portions may be compared with each other at the position within the multiple portions corresponding to the defect in a block-to-block fashion to determine which of the multiple portions is different than the others. In this manner, block-to-block defect relocation may be performed by focusing only on the defective pixel area in the portions of the inspector data or additional inspector image(s). The multiple portion that is different from the others is then determined as the multiple portion containing the defect.

In another embodiment, the position of each multiple portion in the review image(s) may be used to determine the position of each multiple portion with respect to the defect review subsystem. An additional review image that contains all of the identical multiple portions may then be generated by the defect review subsystem (e.g., with high resolution and small FOV). Block-to-block comparison of the additional review images generated by the defect review subsystem may then be performed as described above to determine the multiple portion in which the defect is located. In a different embodiment, the block-to-block comparison may be performed using high resolution, small FOV images of the multiple portions generated by the imaging subsystem instead of the defect review subsystem.

Comparing the multiple portions to each other to identify the multiple portion in which the defect is located will be successful when three or more multiple portions have been found. However, when only two multiple portions have been identified, the multiple portion in which the defect is located cannot be determined from a comparison between the two multiple portions. In particular, both of the multiple portions will be different from each other (since only one contains the defect and therefore the other does not). In this case, the inspector data and possibly other defect information that was requested from the inspection tool may be used to determine which multiple portion contains the defect. For example, the defect information may indicate that the defect has a higher grey level than the background. In such an example, the defect appears brighter than the background. As such, the defect pixels of these two multiple portions may be compared, and the multiple portion that shows brighter pixels at the position corresponding to the defect compared to the background is determined as the block in which the defect is located. In another embodiment, because the grey level and contrast of the optical images are directly linked to the illumination wavelength and illumination mode, the method may include normalizing the grey levels and contrast of the inspector image(s) and review image(s) before using the defect grey level and contrast information to determine the block containing the defect.

As described above, the inspector data may include one or more additional inspector images. In one such embodiment, the method embodiments described herein include comparing the multiple portions with the additional inspector image(s) at the position of the defect illustrated in the additional inspector image(s) to identify the multiple portion in which the defect is located. For instance, the characteristics of the multiple portions at the position of the defect may be compared to the characteristics of the inspector data at the position of the defect. The multiple portion that has characteristics at the position of the defect that are most similar to the characteristics of the inspector data may be determined to be the multiple portion in which the defect is located. For instance, as shown in FIG. 2, in additional inspector image 14, the defect appears as a relatively bright spot. Therefore, the multiple portion that also contains a relatively bright spot at the corresponding position may be determined to be the multiple portion in which the defect is located. In this embodiment, the multiple portion images that are compared to the inspector data may be low resolution images or high resolution images. High resolution images of the multiple portions may be generated by the imaging subsystem or the defect review subsystem.

In another embodiment, the method includes verifying the position of the defect within the portion by acquiring one or more other images (i.e., additional review) image(s)) at the position of the defect within the portion. An image type of the review image(s) is different than an image type of the additional review images. For example, the review image(s) may be optical image(s), and the additional review image(s) may be SEM image(s). In another example, the review image(s) may be large FOV image(s), and the additional review image(s) may be small FOV images. The review image(s) may be acquired by the imaging subsystem, and the additional review image(s) may be acquired by the imaging subsystem or the defect review subsystem.

The method embodiments described above involve determining a "local" position of the defect (i.e., a position of the defect within the review image). However, the position of the defect with respect to the FOV of the defect review subsystem may also be determined. In one embodiment, therefore, the method includes determining a position of the defect with respect to the defect review tool from the position of the defect within the portion of the review image(s) such that the defect can be positioned within a FOV of the defect review tool.

In one such embodiment, the position of the specimen with respect to the imaging subsystem may be determined when the specimen is disposed upon a stage coupled to the imaging subsystem (e.g., prior to defect relocation). Therefore, the position of the review image of the specimen can be determined with respect to the specimen as a whole or with respect to the imaging subsystem based on the position of the specimen with respect to the imaging subsystem. In this manner, the position of the defect can be determined with respect to the specimen or with respect to the imaging subsystem.

This positional information can then be used to determine a position of the defect with respect to a FOV of the defect review subsystem. For instance, the positional relationship between the imaging subsystem and the defect review subsystem may be predetermined (e.g., by prior measurements and/or calibration), and the position of the defect with respect to the imaging subsystem can be used to determine the position of the defect with respect to the FOV of the defect review subsystem based on this positional relationship. In another instance, after defect relocation, the defect review subsystem or a processor coupled to the defect review subsystem may be configured to determine a position of the specimen with respect to the defect review subsystem. Such a positional relationship may be used to align the specimen with respect to the defect review subsystem or to account for variations in the specimen position after movement from the imaging subsystem FOV to the defect review subsystem FOV. In this manner, the position of the defect with respect to the specimen and this positional relationship can be used to determine the position of the defect with respect to the FOV of the defect review subsystem.

Although the method embodiments are described herein with respect to a defect to be reviewed, it is to be understood that the methods may include relocating more than one defect on a specimen. In addition, the defect relocation results for one or more defects may be used in combination with defect coordinates reported by the inspection tool to determine the position of other defects on the specimen with respect to the defect review subsystem. Furthermore, the method embodiments may include any other step(s) described herein.

Unlike previously used methods and systems for automatic defect location (ADL), which are described further in the "Description of the Related Art" section above, the embodiments of the methods described herein do not include redetecting the defects during the defect review process. Instead, the position of the defect is "relocated" by correlating inspector image(s) with a portion of review image(s). The correlation does not involve matching only the defect in the images.

Instead, the images are correlated by using additional information about the specimen to accurately determine the position of the defect within review image(s) in both the x and y dimensions. In addition, by using information that has characteristics in the x and y dimensions, any variation in the angle of rotation of the specimen between inspection and defect review may be detected and corrected. Therefore, the methods described herein can be used to detect and correct any type of spatial variation in the defect location between the inspection tool and the defect review tool.

Accordingly, the method embodiments described herein have a number of advantages over the previously used methods. For example, the accuracy of the embodiments of the methods described herein is independent of the defect coordinate accuracy of an inspection tool. In particular, since the methods described herein include correlating features of inspector image(s) with features of review image(s), the success of the defect relocation is not dependent on the coordinates of the defect reported by the inspection tool. More specifically, the FOV of the imaging subsystem of the defect review tool can be adjusted based on the expected inaccuracy of the reported coordinates from the inspection tool, and since the defect is not redetected in the methods described herein, the effect of the FOV on the review image(s) of the defect will not affect the accuracy of the method embodiments. In addition, the methods described herein involve close coupling of information and images between the inspection tool and the defect review tool.

The method embodiments described herein are, therefore, more accurate for defect relocation during a defect review process than previously used methods. For instance, the method embodiments described herein are capable of substantially higher ADL success rates with high confidence that the located defects are actually the defects reported by the inspection tool. In contrast, previously used methods use review image(s) to redetect defects, and many times defects different from the ones that are reported by the inspection tool are detected on the review tool.

Furthermore, the methods described herein are also capable of relocating defects that cannot be imaged by electron beam based defect review subsystems such as defects that are located below the upper surface of the specimen (e.g., previous layer defects or completely subsurface defects such as voids and inclusions). In addition, if the successfully relocated defects are not imaged by an electron beam based defect review subsystem, then the relocated defects may be classified as previous layer or non-surface defects. Such relocation and classification of defects that are not visible in SEM images is important such that the defects can be examined in other tools such as a focused ion beam (FIB) tool or other failure analysis tool.

The methods described herein are also capable of relocating defect types that may be difficult to relocate successfully using SEM images such as low contrast defects, defects that exhibit signals that may be overwhelmed by unpredictable noise, defects that are too small to be imaged in low resolution SEM images, and defects that are reported due to color variations. In particular, since the methods described herein utilize background pattern information instead of or in addition to defect information to perform defect relocation, the methods are not limited by defect types, defect sizes, and defects that are not visible to a SEM.

Moreover, the method embodiments described herein are not limited by the parameters of the imaging subsystem used to image the specimen during defect locating. In particular, as described above unlike previously used methods for defect redetection, an image of the defect itself is not required to relocate the defect during defect review. As such, the method embodiments described herein do not depend on the ability of the imaging subsystem to image a defect. Such independence from the defect imaging ability of the imaging subsystem is particularly advantageous for defects that are difficult to image such as low contrast defects. In addition, since the method embodiments described herein do not depend on redetection of the defect, the method embodiments described herein are not limited by other parameters involved in defect redetection such as data processing parameters. Therefore, the method embodiments described herein are capable of relocating a defect during a defect review process with higher accuracy than previously used methods.

A further advantage of the embodiments described herein is that since the methods can use an optical imaging subsystem to locate a defect in a defect review process, these methods do not cause charging and/or contamination of the specimen during defect locating. In particular, using an optical imaging subsystem instead of an electron beam subsystem to determine a location of a defect prevents carbonization of contamination already present on the specimen. In addition, since a relatively large FOV optical imaging subsystem can be used to perform defect relocation, the specimen does not have to be subjected to exposure to an electron beam twice: once during defect relocation and again during defect review as in previously used methods. Furthermore, since defect relocation using an electron beam subsystem typically includes exposing the specimen to a relatively high landing energy and beam current such that a large FOV on the specimen can be imaged without substantially reducing the throughput of the defect review process, the electron beam exposure of the specimen that has the largest potential for damaging the specimen is eliminated by the methods described herein. Since the exposure of the specimen to the electron beam during actual defect review is typically performed with a much lower landing energy and beam current (since a much smaller FOV image is generated), damage of the specimen due to defect review processes is substantially eliminated (or at least minimized) by the method embodiments described herein.

The method embodiments described herein also do not reduce the throughput of the defect review process. For instance, all of the steps of the method embodiments described herein can be performed relatively quickly. In particular, all of the steps of the method embodiments except for the acquisition of the review image(s) by the imaging subsystem involve data processing. The throughput of the data processing steps is only limited by the performance of the components used to perform the data processing. In addition, since the acquisition of the review image(s) by the imaging subsystem may involve optical imaging, this step of the method embodiments also has a relatively high throughput. Furthermore, since the methods described herein do not involve defect redetection, the methods described herein eliminate a number of imaging and processing steps that might otherwise reduce the throughput of the defect review process. Moreover, the methods described herein can be completely automated. Such automation also contributes to the high throughput and ease of use of the methods described herein.

Program instructions implementing methods such as those described herein may be transmitted over or stored on a carrier medium. The carrier medium may be a transmission medium such as a wire, cable, or wireless transmission link. The carrier medium may also be a storage medium such as a read-only memory, a random access memory, a magnetic or image acquisition disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

The program instructions may be executable on a processor that may be included in a computer system. The computer system may take various forms, including a personal computer system, mainframe computer system, workstation, image computer or any other device known in the art. In general, the term "computer system" may be broadly defined to encompass any device having one or more processors, which executes instructions from a memory medium. The processor may be further configured as described herein.

Figure 11:
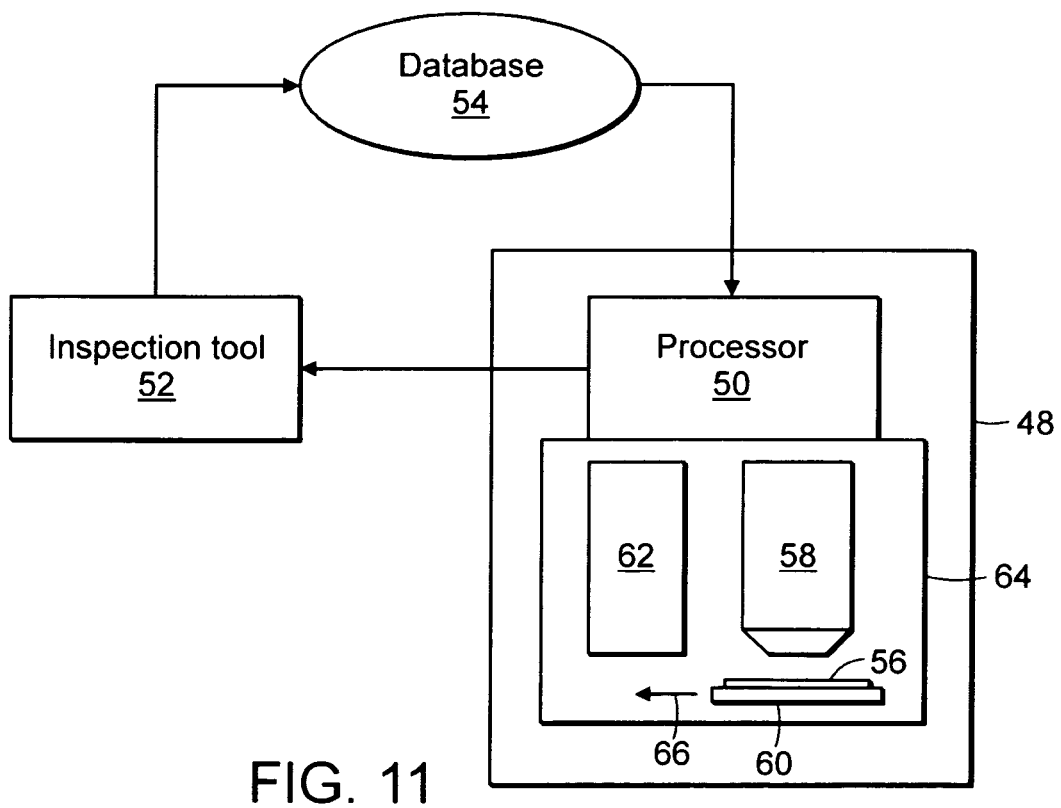
FIG. 11 is a schematic diagram illustrating a side view of one embodiment of a defect review tool configured to locate a defect in a defect review process and one embodiment of a system configured to locate a defect in a defect review process.

Another embodiment relates to a defect review tool that is configured to locate a defect in a defect review process. As will be obvious based on the description of the defect review tool embodiments provided herein, the defect review tool embodiments have all of the advantages of the method embodiments described above. One embodiment of such a defect review tool is illustrated in FIG. 11. As shown in FIG. 11, defect review tool 48 includes processor 50. Processor 50 is configured to acquire inspector image(s) and inspector data from inspection tool 52. The inspector image(s) illustrate an area on a specimen in which a defect to be reviewed is located. The inspector image(s) may include one or more BF images, one or more DF images, one or more laser DF images, one or more SEM images, or some combination thereof. The inspector data indicates a position and features of the defect within the area. The inspector data may include one or more additional inspector image(s) that illustrate the position and the features of the defect within the area. The inspector image(s) and inspector data may be any other images described further herein. For instance, in one embodiment, the inspector image(s) illustrate patterned features on the specimen, and the inspector data includes additional inspector image(s) that do not illustrate the patterned features on the specimen.

Processor 50 may be configured to acquire the inspector image(s) and inspector data from inspection tool 52 in a number of ways. For example, processor 50 may be coupled to one or more components of inspection tool 52 by a transmission medium (not shown). The transmission medium may include any suitable transmission medium known in the art and may include "wired" and "wireless" transmission media. The one or more components of inspection tool 52 to which processor 50 are coupled may include a processor and/or a storage medium (not shown) of inspection tool 52. In one such embodiment, processor 50 may send a request for the inspector image(s) and inspector data to a processor of inspection tool 52. The processor of the inspection tool may then retrieve the inspector image(s) and inspector data from a storage medium of the inspection tool. The processor of the inspection tool may also send the inspector image(s) and inspector data to processor 50. In this manner, processor 50 may receive inspector image(s) and inspector data from the inspection tool across the transmission medium, which functions as a data stream. In addition, processor 50 may receive only the inspector image(s) and inspector data that are requested. As such, processor 50 may not receive all of the images that were generated by the inspection tool during inspection of the specimen. Processor 50 may also request and receive defect and other information such as that described herein in a similar manner.

In this manner, the defect review tool and the inspection tool, in combination, may be configured as an information on-demand system. In other words, during the defect review process run time, the defect review tool sends a request to the inspection tool for specific defect information (e.g., defect patch images, features, polarity, size, region, etc.). The inspection tool may also be configured to send a request to the defect review tool for information that can be used to improve performance of the inspection tool (e.g., defect review subsystem images of the defects, material information of the defects, etc.). Examples of inspection system setup techniques are illustrated in U.S. Patent Application Publication No. 2004/0038454 to Coldren et al., which is incorporated by reference as if fully set forth herein. The methods described herein may include any step(s) described in this publication. In addition, the systems described further herein may be further configured as described in this publication.

In some embodiments, processor 50 is configured to identify the defect to be reviewed using information within database 54. The information was generated by inspection tool 52. In this manner, the inspection tool generated information in database 54 that can be accessed by a processor coupled to a defect review tool. Database 54 may be configured as a defect database. In this manner, the defect database may include inspection results from inspection tool 52 and possibly other inspection tools that are also coupled to the database. Alternatively, database 54 may be configured as a fab database. In this manner, the fab database may include inspection results from inspection tool 52 and possibly other inspection tools that are coupled to the database in addition to information generated by other metrology tools, defect review tools, defect characterization tools, processing tools, etc. located within a fab and coupled to the fab database. In either example, the inspection tool may be configured to automatically send the inspection results to the database upon completion of an inspection process. The inspection tool may be coupled to the database in any manner known in the art. In addition, database 54 may have any suitable configuration known in the art. The inspection results may be further configured as described herein (e.g., as a KLARF file).

Processor 50 may be configured to access the information in the database in any manner known in the art. For instance, the processor may be coupled to the database in any manner known in the art. In addition, processor 50 may be configured to receive or determine an identity of specimen 56 on which one or more defects are to be reviewed. Processor 50 may use the identity of the specimen or any other such information to identify the corresponding inspection results in database 54.

The inspection results may indicate which defects on the specimen are to be reviewed. For instance, selection of the defects to be reviewed ("defect sampling") may be performed by the inspection tool. In this manner, the defects that are to be reviewed on specimen 56 may be indicated in the inspection results accessed by the processor. Alternatively, defect sampling may be performed by processor 50 based on the inspection results accessed from the database. Defect sampling may be performed according to any method known in the art. In this manner, the processor may be configured to identify the defect that is to be reviewed based on the defect sampling results. In addition, inspection tool 52 or processor 50 may be configured to group the defects selected for review into one or more categories prior to the defect review process. In this manner, the processor may use the categories of the defect groups to dynamically determine the review run sequence.

Defect review tool 48 also includes imaging subsystem 58 that is configured to acquire review image(s) of specimen 56 proximate the position of the defect indicated in the inspector data. Imaging subsystem 58 is configured as an optical subsystem in one embodiment. Imaging subsystem 58 is configured to acquire low resolution, large FOV images of specimen 56. Imaging subsystem 58 may or may not also be configured to generate high resolution, small FOV images of specimen 56. Imaging subsystem 58 may be further configured as described herein. The review image(s) may include one or more BF images, one or more DF images, one or more laser DF images, one or more SEM images, or some combination thereof. As shown in FIG. 11, defect review tool 48 may include stage 60 on which specimen 56 is disposed during imaging by imaging subsystem 58. Stage 60 may include any suitable mechanical or robotic assembly known in the art.

Processor 50 is also configured to identify a portion of the review image(s) that corresponds to the inspector image(s). The processor may be configured to identify the portion of the review image(s) that corresponds to the inspector image(s) as described herein. For instance, in one embodiment, the processor is configured to identify the portion of the review image(s) that corresponds to the inspector image(s) by comparing all patterned features illustrated in the inspector image(s) with patterned features illustrated in different portions of the review image(s). In another embodiment, the processor is configured to identify the portion of the review image(s) that corresponds to the inspector image(s) by comparing all patterned features and defect features illustrated in the inspector image(s) with patterned features and defect features illustrated in different portions of the review image(s).

In some embodiments, the processor is configured to identify the portion of the review image(s) that corresponds to the inspector image(s) by determining if multiple portions of the review image(s) correspond to the inspector image(s). In one such embodiment, the processor is also configured to compare the multiple portions with each other at the position indicated in the inspector data to identify the multiple portion in which the defect is located. In another such embodiment, the inspector data includes additional inspector image(s). In such an embodiment, the processor may be configured to compare the multiple portions with the additional inspector image(s) at the position illustrated in the additional inspector image(s) to identify the multiple portion in which the defect is located.

Processor 50 is further configured to determine a position of the defect within the portion of the review image(s) using the inspector data. Processor 50 may be configured to determine the position of the defect within the portion of the review image(s) as described herein. For instance, the defect relocation may be performed by correlating the position of the defect within the patch image from the inspection tool to a position within the low resolution image generated by the imaging subsystem of the defect review tool.

Defect review tool 48 also includes defect review subsystem 62 that is configured as a SEM in one embodiment. The SEM may have any suitable configuration known in the art. For example, the SEM may be configured as one of the e-beam subsystems included in the eDR5000 system, the eCD-1 system, and the eS25 and eS30 systems, which are commercially available from KLA-Tencor, San Jose, Calif. Electron beam based defect review subsystems are advantageous for defect review since they provide the highest image quality currently available in addition to high resolution and high contrast images. However, the defect review tool may include any other defect review subsystem known in the art such as a high resolution optical imaging subsystem.

As shown in FIG. 11, imaging subsystem 58 and defect review subsystem 62 may be disposed within chamber 64. Chamber 64 is preferably a vacuum chamber if defect review subsystem 62 is configured as a SEM. However, in other embodiments, imaging subsystem 58 may be disposed outside of chamber 64 but within defect review tool 48.

In one embodiment, processor 50 is configured to determine a position of the defect with respect to defect review subsystem 62 from the position of the defect within the portion of the review image(s) such that the defect can be positioned within a FOV of defect review subsystem 62. The processor may be configured to determine the position of the defect with respect to defect review subsystem 62 as described herein. In another embodiment, the imaging subsystem is configured to acquire additional review image(s) at the position of the defect within the portion. In one such embodiment, an image type of the review image(s) is different than an image type of the additional review image(s). In such embodiments, the processor may be configured to verify the position of the defect within the portion using the additional review image(s). The additional review image(s) may be acquired as described herein.

Defect review tool 48 may be configured to move specimen 56 in direction 66 from a position under imaging subsystem 58 such that the defect on specimen 56 is positioned within a FOV of defect review subsystem 62. For instance, processor 50 may be coupled to stage 60 in any manner known in the art. In addition, processor 50 may be configured to control stage 60 based on the determined position of the defect with respect to the defect review subsystem such that the defect is positioned within the FOV of the defect review subsystem. In this manner, imaging subsystem 58 and defect review subsystem 62 are coupled to a common stage.

Processor 50 may be configured to perform any other defect review related functions known in the art. For instance, processor 50 may be configured to classify the defects that are reviewed. In some embodiments, processor 50 may be configured to use more than one image for defect classification. In one such embodiment, defect classification may be performed using the inspector image(s), the review image(s), the image(s) generated by the defect review subsystem of the defect review tool, or some combination thereof. The processor may also be configured to use any other information about the defect generated by the inspection tool, the imaging subsystem, and/or the defect review subsystem for defect classification. In addition, the processor may be configured to classify defects using any methods and/or algorithms known in the art. The processor and the defect review tool may also be configured for automatic defect classification (ADC).

Processor 50 may also be configured to generate output that includes results of the defect review process. The output may include, for example, one or more of the inspector image(s), one or more of the review image(s), one or more images generated by the defect review subsystem, defect classification information such as defect material information, an optimized or altered recipe for both the inspection tool and/or the defect review tool, or any combination thereof. The output may be generated in any format such as a KLARF file or any other suitable file known in the art.

The defect review tool may also be configured to have additional functionality. For instance, the defect review tool may be configured to determine a composition of a defect that is reviewed. In one such example, the defect review tool may be configured to perform electron dispersive x-ray (EDX) spectroscopy of defects on the specimen. For instance, if the defect review subsystem is configured as an electron beam based subsystem, then the defect review subsystem may also be configured to perform EDX. Such a defect review subsystem may have any appropriate configuration known in the art. Each of the embodiments of the defect review tool described above may be further configured as described herein.

An additional embodiment relates to a system configured to locate a defect in a defect review process. One such embodiment of a system is illustrated in FIG. 11. In this embodiment, the system includes inspection tool 52 that is configured to generate inspector image(s) that illustrate an area on a specimen in which a defect to be reviewed is located and inspector data that indicates a position and features of the defect within the area. The system also includes defect review tool 48 that is configured to acquire the inspector image(s) and the inspector data from inspection tool 52. The defect review tool is also configured to generate review image(s) of specimen 56 proximate the position indicated in the inspector data and to identify a portion of the review image(s) that corresponds to the inspector image(s). In addition, the defect review tool is configured to determine a position of the defect within the portion of the review image(s) using the inspector data. The system, the inspection tool, and the defect review tool may be further configured as described herein. The system embodiment described above has all of the advantages of the method embodiments described above.

Figure 12:
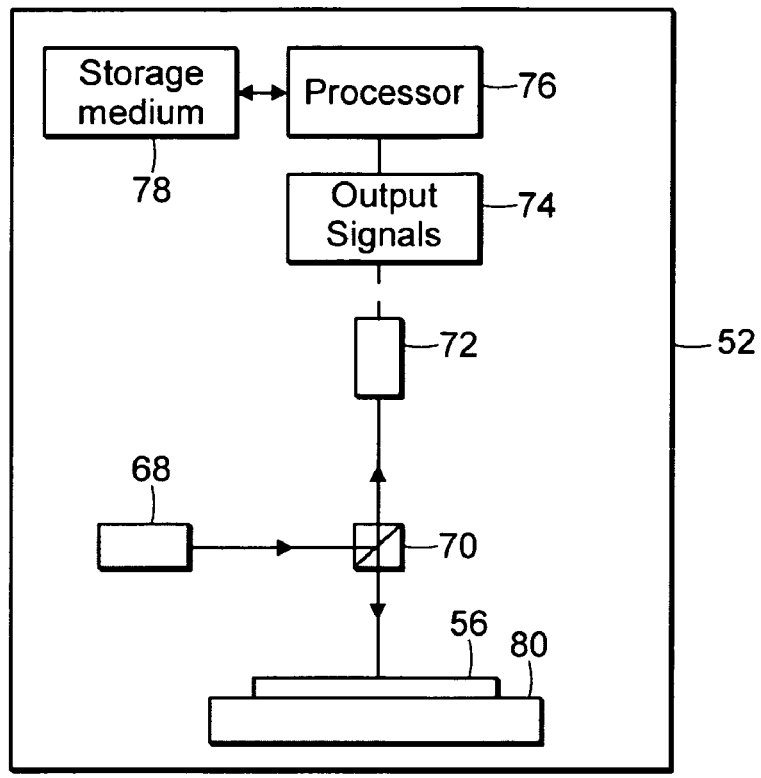
FIG. 12 is a schematic diagram illustrating a side view of one embodiment of an inspection tool that may be included in an embodiment of a system described herein.

FIG. 12 illustrates one embodiment of inspection tool 52 that may be included in a system as described above. Inspection tool 52 includes light source 68. Light source 68 may include any appropriate light source known in the art. In addition, light source 68 may include a broadband light source, a multiple wavelength (polychromatic) light source, or a single wavelength (monochromatic or near-monochromatic) light source. Light from light source 68 is directed to beam splitter 70. Beam splitter 70 may include any suitable optical component known in the art. Beam splitter 70 is configured to direct the light from light source 68 to specimen 56. As shown in FIG. 12, beam splitter 70 is configured to direct the light from the light source to specimen 56 at a substantially normal angle of incidence. However, in other embodiments, beam splitter 70 or a different optical component (not shown), which may be used in place of beam splitter 70, may be configured to direct the light from light source 68 to specimen 56 at an oblique angle of incidence. In some embodiments, inspection tool 52 may be configured to direct light from light source 68 to specimen 56 at different angles of incidence simultaneously or sequentially.

Light reflected from specimen 56 may pass through beam splitter 70 to detection subsystem 72. In this manner, the light that is reflected from the specimen is detected by detection subsystem 72. Detection subsystem 72 may include any suitable detector known in the art. For example, detection subsystem 72 may include an array detector such as a charge coupled device (CCD) camera or a time delay integration (TDI) camera. In this manner, the detection subsystem may generate output signals 74 that can be used to generate an image of specimen 56. In particular, processor 76 may be coupled to detection subsystem 72 in any manner known in the art such that the processor can receive output signals 74 from detection subsystem 72.

Processor 76 may also be configured to generate images of specimen 56 using output signals 74. The images of the specimen generated by processor 76 may include inspector image(s) that illustrate an area on the specimen in which a defect to be reviewed is located. The processor may also be configured to generate inspector data that illustrates a position and features of the defect within the area. Processor 76 may be configured to store the inspector image(s) and the inspector data in storage medium 78. Therefore, upon receiving a request from a defect review tool (not shown in FIG. 12) for the inspector image(s) and the inspector data, processor 76 may be configured to retrieve the inspector image(s) and the inspector data from storage medium 78 and to send the inspector image(s) and the inspector data to the defect review tool. Processor 76 may be coupled to the defect review tool in any manner known in the art (e.g., by a transmission medium).

Inspection tool 52 may include any other components known in the art. For example, as shown in FIG. 12, the inspection tool may include stage 80 on which specimen 56 is disposed during inspection. Stage 80 may include any suitable mechanical or robotic assembly known in the art. Stage 80 may also be configured to move specimen 56 during inspection such that the light directed to the specimen by beam splitter 70 can scan across the specimen. The inspection tool may also include one or more additional optical components (not shown). The one or more additional optical components may include any suitable optical components known in the art such as an objective lens, a collector lens, one or more polarizing components, one or more light filtering components, etc.

As described above, inspection tool 52 is configured to detect light reflected from specimen 56. In this manner, inspection tool 52 is configured as a BF inspection tool. In addition, inspection tool 52 is configured to generate images of specimen 56. Therefore, inspection tool 52 is configured as a BF imaging inspection tool. However, in other embodiments, inspection tool 52 may be configured to detect light scattered and/or diffracted from specimen 56. In this manner, inspection tool 52 may be configured as a DF inspection tool. The DF inspection tool may also be configured to generate images of the specimen.

In further embodiments, the inspection tool may be configured to inspect a specimen using one or more selectable modes. For instance, the inspection tool may be configured to have BF and DF capabilities, and the mode that is used to inspect a specimen may be selected based on, for example, characteristics of the specimen and/or characteristics of the defect of interest. In another instance, the inspection tool may be configured for deep ultraviolet (DUV) BF inspection, ultraviolet (UV) BF inspection, UV DF inspection, or some combination thereof. In addition, the inspection tool may be configured for patterned wafer inspection, bare (or unpatterned) wafer inspection, or both patterned and unpatterned wafer inspection. In an alternative embodiment, the inspection tool may be configured for non-optical inspection. In one such embodiment, the inspection tool may be configured as an electron beam based inspection tool. Such an electron beam based inspection tool may have any suitable configuration known in the art.

Figure 13:
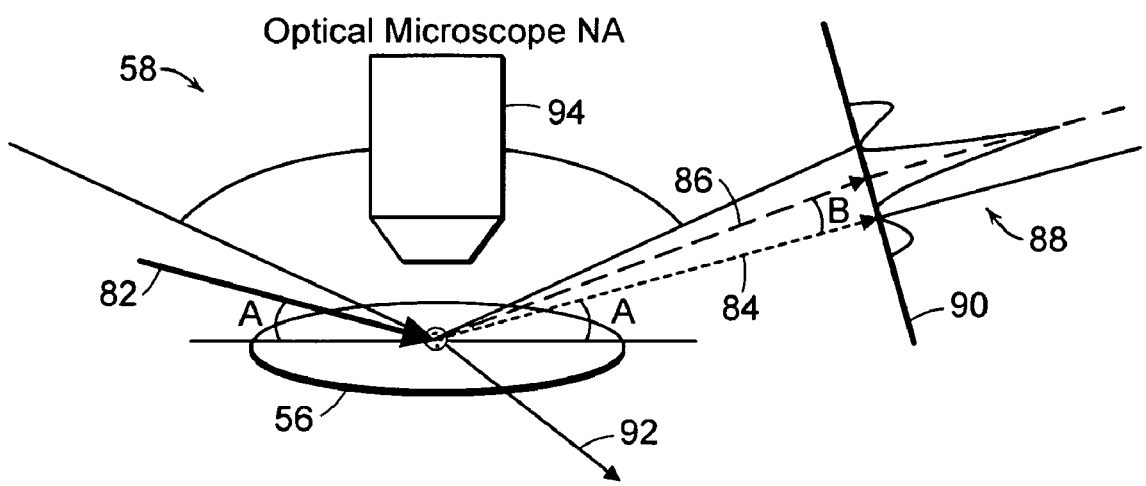
FIG. 13 is a schematic diagram illustrating a side view of one embodiment of an imaging subsystem that may be included in an embodiment of a defect review tool described herein.

FIG. 13 illustrates one embodiment of an imaging subsystem that may be included in the defect review tool embodiments described herein. This embodiment of an imaging subsystem may be particularly suitable for a specimen on which a dense array of patterned structures is formed. In this embodiment, imaging subsystem 58 includes an illumination subsystem (not shown) configured to direct light 82 to specimen 56 at oblique angle of incidence, A. In one example, the illumination subsystem may include a light source such as a relatively high brightness UV source. One example of such a light source may be a laser. However, the illumination subsystem may include any other suitable light source known in the art. The illumination subsystem may also include any other suitable optical components known in the art coupled to the light source.

As shown in FIG. 13, light 84 is specularly reflected from specimen 56 at angle, A, which is equal to the angle of incidence. Light may also be diffracted from patterns on specimen 56. For example, first order light 86 diffracted from specimen 56 may propagate from the specimen at a different angle than that of the specularly reflected light. In particular, the first order light may propagate along a direction at an angle, B, with respect to the specularly reflected light. The angle, B, is proportional to the technology node. In particular, angle, B, tends to decrease as the technology node decreases. Intensity distribution 88 of the light diffracted from specimen 56 at image plane 90 indicates the amount of light scattered from the patterns on the specimen into different orders. Light 92 may also be diffracted by the pattern on the specimen out of the plane of incidence.

As shown in FIG. 13, imaging subsystem 58 may include detection subsystem 94 that is arranged to detect light scattered from specimen 56. In some embodiments, the numerical aperture, NA, of the imaging subsystem may be selected such that the light detected by detection subsystem 94 does not include the light reflected from the specimen and a substantial portion of the light diffracted from the specimen. In other words, the NA of the imaging subsystem may be selected such that the detection subsystem does not collect the pattern signal from the specimen. In this manner, a pattern formed on the specimen may not be resolved in review image(s) formed by detection subsystem 94. In particular, as shown in FIG. 13, the NA of the imaging subsystem may be selected such that the detection subsystem collects light diffracted into only one higher order by the pattern on the specimen. In one such example, the NA of the imaging subsystem may be selected to be less than 0.8.

By selecting the imaging subsystem NA such that the pattern signal is not collected, the review image(s) acquired by the imaging subsystem may have substantially high defect contrast. In addition, the optical imaging subsystem shown in FIG. 13 may produce review image(s) having better contrast than a SEM based imaging subsystem since the pattern from the specimen can be optically filtered by the optical imaging subsystem. The embodiment of the imaging subsystem shown in FIG. 13 may be particularly suitable for use as an imaging subsystem of a defect review tool that is to be used to review defects detected by SEM based inspection.

Although one particular optical imaging subsystem configuration is shown in FIG. 13, it is to be understood that the optical imaging subsystem can have a number of different configurations. For example, the optical imaging subsystem may be configured to use an optical technique such as BF and/or DF optical microscopy on the defect review tool in parallel with the UV/DUV OM used on the inspection tool. In another example, the optical imaging subsystem may be configured as a DF OM. Such an optical imaging subsystem may also be configured to spatially filter light from the specimen. The spatial filtering may be Fourier filtering or any other spatial filtering. In addition, the Fourier or other spatial filtering may be performed using an analog or digital filter. An analog filter is a spatial filter that is positioned in the light collection path. Digital filtering is performed on the acquired image. In a further example, the optical imaging subsystem may be configured as a UV illumination BF OM capable of high magnification and a relatively high NA (e.g., an NA greater than about 0.9).

As will be understood based on the embodiments described above, a number of different combinations of inspection tool configurations, imaging subsystem configurations, and defect review subsystem configurations are within the scope of the description provided herein. For instance, in one embodiment, a DUV inspection tool, a SEM imaging subsystem, and a SEM defect review subsystem may be included in a system. In such embodiments, a SEM imaging subsystem may be used for better resolution of the features on the specimen. In addition, the imaging subsystem may also be used as the defect review subsystem. In these embodiments, the defect location may be determined by correlating inspector image(s) and inspector data (e.g., one or more patch images and defect information) with review image(s) generated by the SEM imaging subsystem. Such a correlation may be performed using a block-to-block comparison as described further above. In addition, in such embodiments, classification of the defect may be performed using multiple images including, for example, the review image(s) in combination with the inspector image(s).

In a different embodiment, a UV BF inspection tool, an optical imaging subsystem (configured for BF and/or DF (such as Edge Contrast mode in which complementary apertures are included in the illumination and light collection paths)), and a SEM defect review subsystem may be included in a system. For example, the inspection tool may include one of the 236x or 237x BF inspection tools commercially available from KLA-Tencor, the optical imaging subsystem may be configured as the AIT Fusion UV system or PUMA DF system commercially available from KLA-Tencor and possibly configured for visible imaging, and the defect review subsystem may be configured as a SEM. In such an embodiment, the defect location may be determined by correlating a patch image and defect information generated by the inspection tool with review image(s) generated by the optical imaging subsystem. Such a correlation may be performed using a block-to-block comparison as described further above. In addition, in such embodiments, classification of the defect may be performed using multiple images of the defect including, for example, the SEM image generated by the defect review subsystem, the patch image generated by the inspection tool, and the image generated by the optical imaging subsystem.

In another embodiment, a DF imaging inspection tool, an optical imaging subsystem configured for oblique DF laser based imaging (which may include a relatively high power UV laser), and a SEM defect review subsystem may be included in a system. In such an embodiment, the defect location may be determined by correlating images generated by the DF inspection tool and the optical imaging subsystem (possibly in combination with Fourier filtering performed optically or electronically). In addition, in such embodiments, classification of the defect may be performed using multiple images of the defect including, for example, the SEM image generated by the defect review subsystem, the patch image generated by the inspection tool, and the image generated by the optical imaging subsystem.

In an additional embodiment, a DF inspection tool such as one of the SP1 and SP2 tools that are commercially available from KLA-Tencor, an optical imaging subsystem configured for oblique DF laser based imaging (which may include a relatively high power UV laser), and a SEM defect review subsystem may be included in a system. In such an embodiment, the defect location may be determined by correlating images generated by the DF inspection tool and the optical imaging subsystem. In addition, in such embodiments, classification of the defect may be performed using multiple images of the defect including, for example, the SEM image generated by the defect review subsystem and the image generated by the optical imaging subsystem.

In yet another embodiment, an electron beam based inspection tool such as the eS3X tool that is commercially available from KLA-Tencor, a SEM imaging subsystem (possibly also configured for voltage contrast imaging), and a SEM defect review subsystem may be included in a system. In such an embodiment, the defect location may be determined by correlating a patch image generated by the electron beam based inspection tool and the image generated by the electron beam imaging subsystem. Such a correlation may be performed in a block-to-block mode as described further herein. In addition, in such embodiments, classification of the defect may be performed using multiple images of the defect including, for example, the patch image generated by the electron beam based inspection tool and the SEM defect review subsystem.

Although the method and system embodiments are described herein with respect to locating a defect in a defect review process, it is to be understood that the methods and systems can be used to locate a defect in other processes. For instance, the methods and systems described herein can be used to locate a defect in any other characterization, metrology, and classification processes. In one such example, the methods and systems can be used to locate a defect in an EDX system that is configured to determine a composition of a defect. In addition, the defect review tool embodiments described herein can be configured to have such characterization, metrology, and classification functions.

Further modifications and alternative embodiments of various aspects of the invention may be apparent to those skilled in the art in view of this description. For example, methods, defect review tools, and systems for locating a defect in a defect review process are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for locating a defect in a defect review process, comprising:
using a processor included in a computer system to perform the steps of:
acquiring an image and data from an inspection tool, wherein the image illustrates an area on a specimen in which a defect to be reviewed is located, and wherein the data indicates a position and features of the defect within the area;
acquiring an additional image of the specimen proximate the position of the defect indicated in the data using an imaging subsystem of a defect review tool;
identifying a portion of the additional image acquired using the imaging subsystem of the defect review tool that corresponds to the image acquired from the inspection tool, wherein said identifying comprises comparing, within a search window in the additional image, the image acquired from the inspection tool with different portions of the additional image acquired using the imaging subsystem of the defect review tool, wherein dimensions of the search window are larger than dimensions of the image, determining if multiple portions within the search window in the additional image correspond to the image, wherein dimensions of each of the multiple portions are the same as the dimensions of the image, and comparing the multiple portions that correspond to the image with each other at the position of the defect indicated in the data to identify the multiple portion in which the defect is located; and
determining a position of the defect within the identified multiple portion of the additional image using the data.

2. The method of claim 1, further comprising identifying the defect using information within a database, wherein the information was generated by the inspection tool.

3. The method of claim 1, wherein the image comprises a bright field image, a dark field image, a laser dark field image, a scanning electron microscope image, or some combination thereof.

4. The method of claim 1, wherein the data comprises one or more other images that illustrate the position and the features of the defect within the area.

5. The method of claim 1, wherein the additional image comprises a bright field image, a dark field image, a laser dark field image, a scanning electron microscope image, or some combination thereof.

6. The method of claim 1, wherein said acquiring the image and the data from the inspection tool is performed by the defect review tool.

7. The method of claim 1, wherein the defect review tool and the inspection tool, in combination, are configured as an information on-demand system.

8. The method of claim 1, wherein the imaging subsystem is configured as an optical subsystem.

9. The method of claim 1, wherein the defect review tool is configured as a scanning electron microscope.

10. The method of claim 1, further comprising determining a position of the defect with respect to the defect review tool from the position of the defect within the identified multiple portion of the additional image such that the defect can be positioned within a field of view of the defect review tool.

11. The method of claim 1, wherein the image illustrates patterned features on the specimen, and wherein the data comprises one or more other images that do not illustrate the patterned features on the specimen.

12. The method of claim 1, wherein said identifying further comprises comparing all patterned features illustrated in the image with patterned features illustrated in the different portions of the additional image.

13. The method of claim 1, wherein said identifying further comprises comparing all patterned features and defect features illustrated in the image with patterned features and defect features illustrated in the different portions of the additional image.

14. The method of claim 1, wherein the data comprises one or more other images, and wherein said identifying further comprises comparing the multiple portions with the one or more other images at the position of the defect illustrated in the one or more other images to identify the multiple portion in which the defect is located.

15. The method of claim 1, further comprising verifying the position of the defect within the identified multiple portion by acquiring one or more other images at the position of the defect within the identified multiple portion, wherein an image type of the additional image is different than an image type of the one or more other images.

16. A defect review tool configured to locate a defect in a defect review process, comprising:
a processor configured to acquire an image and data from an inspection tool, wherein the image illustrates an area on a specimen in which a defect to be reviewed is located, and wherein the data indicates a position and features of the defect within the area; and an imaging subsystem configured to acquire an additional image of the specimen proximate the position of the defect indicated in the data;

wherein the processor is further configured to identify a portion of the additional image acquired by the imaging subsystem of the defect review tool that corresponds to the image acquired by the processor from the inspection tool, wherein identifying the portion of the additional image comprises comparing, within a search window in the additional image, the image acquired from the inspection tool with different portions of the additional image acquired by the imaging subsystem of the defect review tool, wherein dimensions of the search window are larger than dimensions of the image, determining if multiple portions within the search window in the additional image correspond to the image, wherein dimensions of each of the multiple portions are the same as the dimensions of the image, and comparing the multiple portions that correspond to the image with each other at the position of the defect indicated in the data to identify the multiple portion in which the defect is located, and wherein the processor is further configured to determine a position of the defect within the identified multiple portion of the additional image using the data.

17. The defect review tool of claim 16, wherein the processor is further configured to identify the defect using information within a database, and wherein the information was generated by the inspection tool.

18. The defect review tool of claim 16, wherein the image comprises a bright field image, a dark field image, a laser dark field image, a scanning electron microscope image, or some combination thereof.

19. The defect review tool of claim 16, wherein the data comprises one or more other images that illustrate the position and the features of the defect within the area.

20. The defect review tool of claim 16, wherein the additional image comprises a bright field image, a dark field image, a laser dark field image, a scanning electron microscope image, or some combination thereof.

21. The defect review tool of claim 16, wherein the defect review tool and the inspection tool, in combination, are further configured as an information on-demand system.

22. The defect review tool of claim 16, wherein the imaging subsystem is configured as an optical subsystem.

23. The defect review tool of claim 16, further comprising a defect review subsystem configured as a scanning electron microscope.

24. The defect review tool of claim 16, wherein the processor is further configured to determine a position of the defect with respect to a defect review subsystem from the position of the defect within the identified multiple portion of the additional image such that the defect can be positioned within a field of view of the defect review subsystem.

25. The defect review tool of claim 16, wherein the image illustrates patterned features on the specimen, and wherein the data comprises one or more other images that do not illustrate the patterned features on the specimen.

26. The defect review tool of claim 16, wherein the processor is further configured to identify the portion of the additional image that corresponds to the image by comparing all patterned features illustrated in the image with patterned features illustrated in the different portions of the additional image.

27. The defect review tool of claim 16, wherein the processor is further configured to identify the portion of the additional image that corresponds to the image by comparing all patterned features and defect features illustrated in the image with patterned features and defect features illustrated in the different portions of the additional image.

28. The defect review tool of claim 16, wherein the data comprises one or more other images, and wherein the processor is further configured to identify the portion of the additional image that corresponds to the image by comparing the multiple portions with the one or more other images at the position illustrated in the one or more other images to identify the multiple portion in which the defect is located.

29. The defect review tool of claim 16, wherein the imaging subsystem is further configured to acquire one or more other images at the position of the defect within the identified multiple portion, wherein an image type of the additional image is different than an image type of the one or more other images, and wherein the processor is further configured to verify the position of the defect within the identified multiple portion using the one or more other images.

30. A system configured to locate a defect in a defect review process, comprising:

an inspection tool configured to generate an image that illustrates an area on a specimen in which a defect to be reviewed is located and data that indicates a position and features of the defect within the area; and a defect review tool configured to acquire the image and the data from the inspection tool, to generate an additional image of the specimen proximate the position indicated in the data, and to identify a portion of the additional image generated by the defect review tool that corresponds to the image generated by the inspection tool, wherein identifying the portion of the additional image generated by the defect review tool that corresponds to the image generated by the inspection tool comprises comparing, within a search window in the additional image, the image generated by the inspection tool with different portions of the additional image generated by the defect review tool, wherein dimensions of the search window are larger than dimensions of the image, determining if multiple portions within the search window in the additional image correspond to the image, wherein dimensions of each of the multiple portions are the same as the dimensions of the image, and comparing the multiple portions that correspond to the image with each other at the position of the defect indicated in the data to identify the multiple portion in which the defect is located, and wherein the defect review tool is further configured to determine a position of the defect within the identified multiple portion of the additional image using the data.

* * * * *